(12) United States Patent
Muir et al.

(10) Patent No.: US 6,337,385 B1
(45) Date of Patent: Jan. 8, 2002

(54) STAPHYLOCOCCUS PEPTIDES FOR BACTERIAL INTERFERENCE

(75) Inventors: Tom W. Muir, New York, NY (US); Patricia Mayville, Mahwah, NJ (US); Richard P. Novick, New York, NY (US); Ronald Beavis, Winnipeg (CA); Guangyong Ji, Rockville, MD (US)

(73) Assignees: The Rockefeller University; New York University, both of New York, NY (US)

( * ) Notice: Subject to any disclaimer, the term of this patent is extended or adjusted under 35 U.S.C. 154(b) by 0 days.

(21) Appl. No.: 09/339,511

(22) Filed: Jun. 24, 1999

Related U.S. Application Data (60) Provisional application No. 60/090,402, filed on Jun. 24, 1998.

(51) Int. Cl.[7] .................. A61K 38/12; A61K 38/00; C07K 16/00
(52) U.S. Cl. .............. 530/317; 530/331; 530/323; 514/9; 514/11; 514/13; 514/18
(58) Field of Search ................. 514/11, 13, 18, 514/9; 530/331, 317, 318, 311, 323, 324, 322; 424/177

(56) References Cited

U.S. PATENT DOCUMENTS

| 4,310,518 A | * | 1/1982 | Freidinger et al. ........... 424/177 |
| 5,795,958 A | * | 8/1998 | Rao et al. ................... 530/331 |

FOREIGN PATENT DOCUMENTS

| WO | WO 92/06998 | 4/1992 | |
| WO | WO 97/44349 | 11/1997 | |
| WO | 97/44349 | * 11/1997 | ............ C07K/1/00 |
| WO | WO 99/26968 | 6/1999 | |

OTHER PUBLICATIONS

Title: Novel Staphylococcus Peptides for Bacterial Interference.
Balaban, N., et al., *Science* 280:438–440 (1998).
Bax, A. and D.G. Davis, *J.Magn.Reson.* 655:355–360 (1985).
Buice, T.C. and S.J. Benkovic, in *Bioorganic Mechanisms* 1:259–297 (Benjamin, New York, 1966).
Camarero, G.C., et al., *J.Peptide Res.* 51:303–316 (1998).
Chou, T.C. and F. Lippmann, *J. Biol. Chem.* 196:89 (1952).
Ji, G., et al., *Proc. Natl. Acad. Sci. USA* 92:12055–12059 (1995).
Ji, G., et al., *Science* 276:2027–2030 (1997).
Law, S.K., and A. W. Dodds, *Protein Science* 6:263–274 (1997).
Mendal, M. *Tetrahedron Lett.* 33:3077–3080 (1992).
Morfeldt, E., et al., *EMBO J.* 14:4569–4577 (1995).
Muir, T.W., et al., *Chemistry and Biology* 3:817–825 (1996).
Novick, R.P., et al., *Mol.Gen.Genet.* 248:446–458 (1995).
Novick, R.P., et al., *EMBO J.* 12:3967–3975 (1993).
Porter, J.A., et al., *Science* 274:255–259 (1996).
Schnolzer, M., et al., *Int. J. Pept. Protein Res.* 40:180–193 (1992).
Wuthrich, K, *NMR of Proteins and Nucleic Acids* (Wiley, New York, 1986).
Xu, M.–Q., and F.B. Perler, *EMBO J.* 15:5146–5153 (1996).
Ballio et al., 1994, FEBS Letters, 355:96–100.
Hamann et al., 1996, J Org Chem, 61:6594–600.
Fuuchi et al., 1992, J Chem Soc Perkin Trans, 7:875–80.
Mayville et al., 1999, Pro Natl Acad Sci US, 96:1218–23.
Otto et al.,. 1999, FEBS Letters, 450:257–62.
Tsubotani et al., 1993, J Antibiotics, 46:287–93.
Zechel and Kesssler, 1985, Pept Struct Function Proc Am Pep Sym, pp. 507–10.

* cited by examiner

*Primary Examiner*—Karen Cochrane Carlson
*Assistant Examiner*—Rita Mitra
(74) *Attorney, Agent, or Firm*—Klauber & Jackson (57) ABSTRACT

The present invention provides a cyclic peptide comprising the structure:

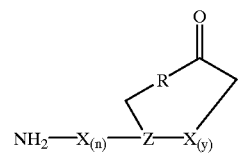

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10. The present invention also provides a cyclic peptide comprising the amino acid sequence of $NH_2$—$X_{(n)}$—Z—$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10. Methods of preparation including a cyclization protocol, and methods of use of the cyclic peptides of the invention are also disclosed.

20 Claims, 6 Drawing Sheets

| AgrDII Peptide Variant | Activation (ED₅₀ nM) Group II Cells | Inhibition (IC₅₀ nM) Group I Cells | Inhibition (IC₅₀ nM) Group II Cells | Inhibition (IC₅₀ nM) Group III Cells |
|---|---|---|---|---|
| Ala 1 (Gly to Ala) | 31 | <1 | None | Not determined |
| Ala 2 (Val to Ala) | 73 | <1 | None | Not determined |
| Ala 3 (Asn to Ala) | None | <1 | None | Not determined |
| Ala 6 (Ser to Ala) | 63 | <<1 | None | Not determined |
| Ala 7 (Ser to Ala) | <1 | <1 | None | Not determined |
| Ala 8 (Leu to Ala) | None | None | None | Not determined |
| Ala 9 (Phe to Ala) | None | None | None | Not determined |

STAPHYLOCOCCUS PEPTIDES FOR BACTERIAL INTERFERENCE

CROSS REFERENCE TO RELATED APPLICATION

The present invention claims priority under 35 U.S.C. §119(e) from Provisional Application Ser. No. 60/090,402, filed Jun. 24, 1998, the disclosure of which is incorporated herein by reference in its entirety.

Throughout this application, various publications are referenced by author and date. Full citations for these publications may be found listed alphabetically at the end of the specification immediately following the Sequence Listing and the claims. The disclosures of these publications in their entireties are hereby incorporated by reference into this application in order to more fully describe the state of the art. The Sequence Listing is provided following the list of references and before the claims.

FIELD OF THE INVENTION

The present invention relates generally to synthetic, cyclic peptides for bacterial interference.

BACKGROUND OF THE INVENTION

*Staphylococcus aureus* (*S. aureus*) is an important pathogen in humans which is now under increasing risk of developing antibiotic resistance to currently available therapeutics. Consequently, there is a pressing need to identify new types of antibiotic agents effective against these drug resistant bacterial strains. The phenomenon of 'bacterial interference' may provide as yet unexplored avenues for the design of these new therapeutics. Bacterial interference refers to the ability of one organism to disrupt the biological functions of another. Until recently this survival process was thought to occur solely through a growth inhibition mechanism (Ji, G., et al., 1997), however a novel type of bacterial interference in *S. aureus* has been described which involves the inhibition of the so-called agr response (Novick, R. P., et al., 1993, Morfeldt, E., et al., 1995). This process is mediated by short secreted peptides containing a putative thiololactone ring structure. Chemical synthesis confirms that the native Agr peptides contain a thiololactone moiety, and that this structure is absolutely necessary for full biological activity. In addition, structure-activity studies are described by the present invention which offer insights into the nature of the agr activation and inhibition mechanisms.

Accessory genes allow bacteria to survive and multiply in plant or animal hosts. In *S. aureus* these virulence factors (cytotoxins and tissue-degrading enzymes) are under the control of the agr locus which contains two divergent promoters, P2 and P3. The RNA transcript from the P3 promoter is responsible for the upregulation of secreted virulence factors as well as the downregulation of surface proteins, the agr response (Novick, R. P., et al., 1993, Morfeldt, E., et al., 1995). There are four genes, agrA-D, in the P2 operon which code for the cytosolic, transmembrane and extracellular components of a density-sensing/autoinduction circuit (Novick, R. P., et al., 1995). The product of the agrD gene is a pro-peptide which is processed and secreted through AgrB, an integral membrane protein. The active AgrD peptide is then thought to bind to the transmembrane receptor coded by the agrC gene. Binding of the AgrD peptide triggers a standard two-component signal transduction pathway in which the AgrC receptor becomes autophosphorylated on a histidine residue leading to subsequent trans-phosphorylation of the AgrA gene product. Phosphorylated AgrA then activates the transcription from the P2 and P3 agr promoters (Novick, R. P., et al., 1995).

*S. aureus* strains can be divided into a least three groups (Ji, G., et al., 1997), each of whose secreted AgrD peptide can activate the agr response within the same group and inhibit the agr response in strains belonging to the other groups. It is the latter effect that constitutes a novel form of bacterial interference (Ji, G., et al., 1997). The AgrD auto-inducing peptides, generated following processing and secretion through AgrB, consist of seven to nine residues. Interestingly, the sequences are highly variable among the groups, although all contain a conserved cysteine residue 5 amino acids from the C-terminus. Mass spectrometric analysis of AgrD peptides isolated from culture supernatants indicated a mass discrepancy of −18 Da compared to the predicted masses based on the peptide sequences (Ji, G., et al., 1995). This observation combined with the presence of the conserved cysteine residue in AgrD peptides, has led to the suggestion that these secreted peptides contain an intramolecular thiol ester linkage between the cysteine sulfhydryl group and the carboxy-terminus (Ji, G., et al., 1997). Consistent with this thiololactone structure, the addition of hydroxylamine to a purified AgrD peptide was observed to abolish its biological activity (Ji, G., et al., 1997).

The inability to isolate significant quantities of secreted AgrD peptides means that very little is known about the biochemistry of the AgrD/AgrC interaction. For example, the potency of the AgrD peptide in either activating (within *S. aureus* strains of the same group) or inhibiting (in *S. aureus* strains from other groups) the agr response is unknown. Equally, it is essential to determine whether the putative thiololactone structure within the AgrD peptides is required for activation of the agr response, inhibition of the agr response or both. The present disclosre provides such elucidation. This study detailed herein confirms the presence of the thiololactone moiety within the AgrD peptides through total chemical synthesis. Having demonstrated synthetic access to the system, more rigorous biochemical and structure-activity studies on the AgrD/AgrC interaction are addressed. The present disclosure further delineates that elimination of the thiol ester component of the cyclic ring structure can destroy activity activating the agr response while preserving (and enhancing) inhibitory activity.

SUMMARY OF THE INVENTION

The present invention provides a cyclic peptide comprising the structure:

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10. The invention also contemplates a peptide composition comprising the provided cyclic peptide and a carrier.

The present invention also provides a cyclic peptide comprising the amino acid sequence of $NH_2-X_{(n)}-Z-X$ $_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10. The invention also contemplates a peptide composition comprising the provided cyclic peptide and a carrier, as well as therapeutic methods for treatment of infection that involve the administration of the pharmaceutical compositions that are and may be prepared in accordance with the teachings of the invention herein. Yet further, the invention extends to methods for the preparation of the cyclic peptide involving a cyclization protocol that is described in further detail herein and is illustrated in Example 1 and in FIG. 1A, and that itself is inventive.

Accordingly, it is a principal object of the present invention to provide a cyclic peptide comprising the amino acid sequence of $NH_2$—$X_{(n)}$—Z—$X_{(y)}$—COOH and a cyclic bond between the Z residue and COOH other than a thioester bond, wherein wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10.

It is a further object of the present invention to provide a cyclic peptide comprising the amino acid sequence of $NH_2$—$X_{(n)}$—Z—$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10, that is devoid of activating activity and which retains inhibitory activity.

It is yet a further object of the present invention to provide a cyclic peptide comprising the amino acid sequence of $NH_2$—$X_{(n)}$—Z—$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10, wherein the bond is a selected from the group consisting of a lactam ring and a lactone ring.

It is a still further object of the present invention to provide a pharmaceutical composition which comprises the provided peptides and a pharmaceutically acceptable carrier.

It is yet another object of the present invention to provide a method for the treatment of an *S. aureus* infection in a subject comprising administering to the subjects the provided pharmaceutical composition in an amount effective to treat the infection in the subject.

It is a still further object of the invention to provide methods for the preparation of the cyclic peptides of the invention that involve a solid phase cyclization protocol as illustrated and described herein.

Other objects and advantages will become apparent to those skilled in the art from a review of the ensuing description which proceeds with reference to the following illustrative drawings.

BRIEF DESCRIPTION OF THE FIGURES

FIGS. 1A–1C. Chemical synthesis of AgrD autoinducing peptides. FIG. 1C. Reverse-phase HPLC of the crude AgrDII reaction mixture. Inset shows the ESMS of the major component in the mixture: expected mass for the AgrDII thiololactone=880.0129 Da (879.9 mass). Both HPLC spectra were obtained using a linear gradient of 0–73% buffer B over 30 minutes (buffer B=CH3CN: H20: trifluoracetic acid; 90:10:1). ESMS was performed on a PE-Sciex API-100 single-quadrupole electrospray mass spectrometer. Calculated masses were obtained using the program MacProMass (Sunil Vemuri and Terry Lee, City of Hope, Duarte, Calif.).

FIGS. 2A–2C. Synthetic thiololactone peptides are biologically active. FIG. 2A and FIG. 2B show representative data for activation and inhibition, respectively, of the agr response by a synthetic thiololactone peptide. Degree of activation/inhibition of the agr response, based on β-lactamase activity (see Table 1), is shown as a plot of Vmax versus peptide concentration.

FIGS. 3A–B. Proposed model for the activation and the inhibition of the agr response.

DETAILED DESCRIPTION

The present invention provides a cyclic peptide comprising the structure:

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10.

The present invention also provides a cyclic peptide comprising the amino acid sequence of $NH_2$—$X_{(n)}$—Z—$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10.

An embodiment of the present invention is a compound comprising the provided peptide, peptidomimetic thereof or polymer thereof.

A further embodiment of the invention extends to a method for the preparation of the present cyclic peptide, which method comprises assembling the linear constituents of the peptide under preparation on a PEGA resin support to form a protected and bound peptide chain; treating the resulting peptide chain to cause deprotection thereof; thereafter treating the deprotected peptide with buffer at a neutral pH for a period of time sufficient to cleave said peptide from said solid phase support and to form the cyclic peptide in object; and recovering the cyclic peptide. More particularly, the method comprises assembling the linear peptide chain corresponding in composition to the said cyclic peptide on to a solid phase resin support containing 3-mercapto-propionamide-polyethylene glycol-poly-($N_1N_4$-dimethacrylamide)(HS-PEGA) to form a protected assembled peptide; treating the protected assembled peptide of the previous step to deprotect the said assembled peptide; treating the deprotected peptide with aqueous buffer at a pH of about 7.0 for a period of time sufficient to form the said cyclic peptide and to cleave the peptide from the solid phase resin support; and recovering the cyclic peptide in object.

Figure 1A:
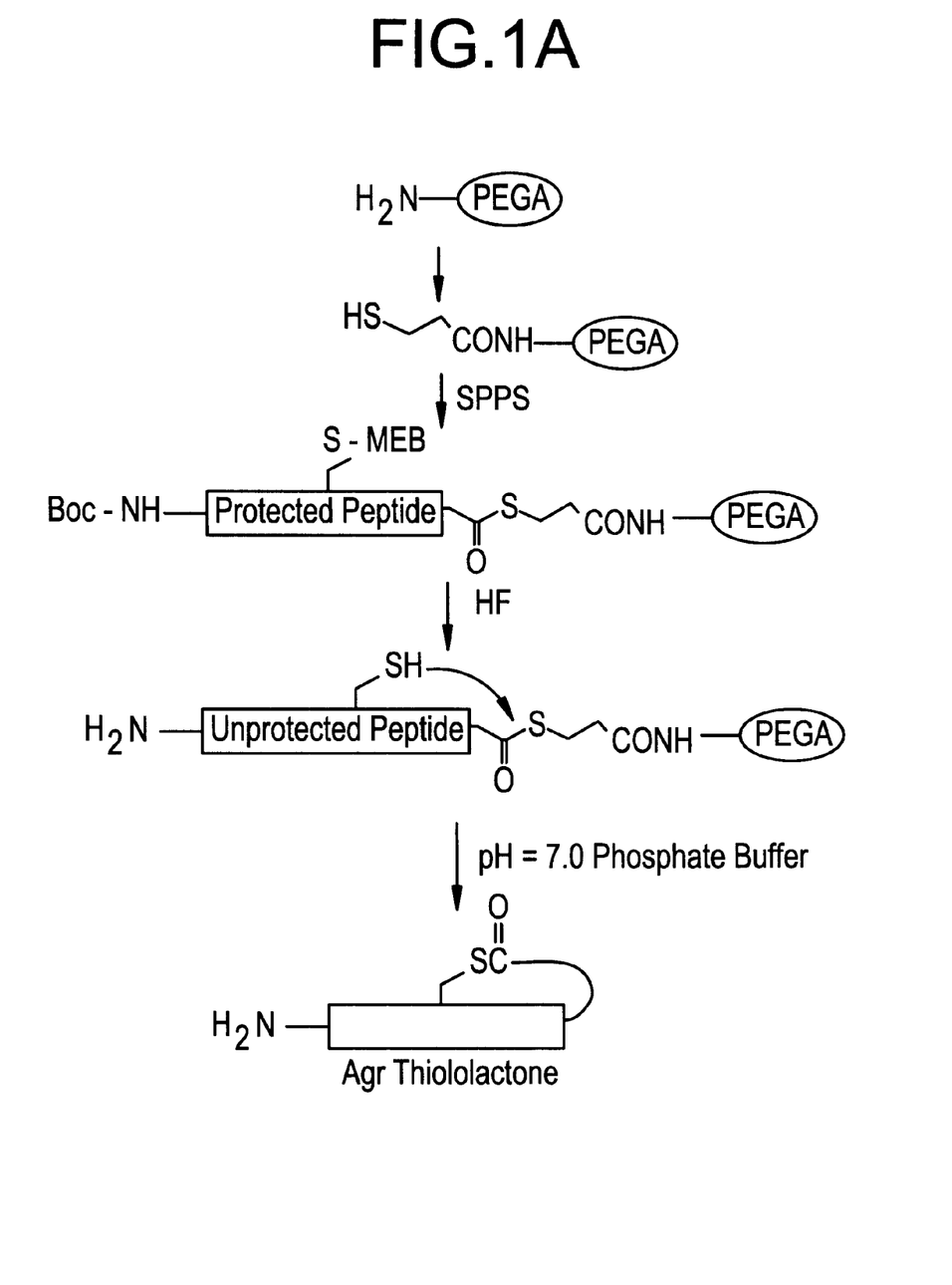
FIG. 1A. Generation of thiololactone peptides via a solid phase intramolecular chemical ligation strategy.

As described in detail in Example 1 and as depicted in FIG. 1A herein, the present method utilizes a solid phase cyclization protocol as its last step in the formation of the inventive cyclic peptides. Also, the method involved the initial preparation of a fully unprotected peptide on a solid support through a reactive thiol ester bond. Accordingly, a representative solid phase resin support suitable for use in the present method may comprise BOC-AA-(linear assembled peptide)-PEGA. Further, the deprotection treatment that follows the assembly of the peptide on the resin support may for example, be performed with HF for a period of time of about 1 hour. Thereafter, the cleavage of the peptide from the support and the formation of the cyclic peptide may be performed with a buffer such as $Na_2PO_4$ and acetonitride. Also, this step is performed for a period of time sufficient to achieve both cleavage and cyclization, which may for example, extend for a period of about 12 hours. Naturally the foregoing reagents and process parameters may vary within the scope of the invention, and the invention is intended to cover such variations within its spirit and scope.

In another embodiment of this invention, the cyclic peptide is capable of inhibiting agr response. In another embodiment of this invention, Z has a side chain comprising oxygen or nitrogen. In another embodiment of this invention, Z presents a functionality capable of cyclizing through a thioether group, an ether group or a carbon-carbon group. In yet another embodiment of this invention, the cyclic bond is a lactam or lactone bond. In still another embodiment, y is 4. According to yet another embodiment of this invention, the peptide has an amino acid sequence that comprises G-V-N-A-X-S-S-L-F (Seq.ID No.:1), G-A-N-A-X-S-S-L-F (Seq.ID No.:2), G-V-A-A-X-S-S-L-F (Seq.ID No.:3), A-V-A-N-X-S-S-L-F (Seq.ID No.:4), G-V-N-A-X-A-S-L-F (Seq.ID No.:5), G-V-N-A-X-S-A-L-F (Seq.ID No.:6), G-V-N-A-X-S-S-A-F (Seq.ID No.:7), and X-S-S-L-F (Seq.ID No. 8). Still, in yet another embodiment of the present invention, the peptide has an amino acid sequence that comprises a hydrophobic amino acid in the carboxy terminal or penultimate carboxyterminal position.

The present invention also provides a pharmaceutical composition comprising the described peptide and a pharmaceutically acceptable carrier. In an embodiment of this invention, the carrier is selected from the group consisting of a diluent, an aerosol, a topical carrier, an aqueous solution, a nonaqueous solution and a solid carrier.

Finally, the present invention provides a method for treating S. aureus infection in a subject comprising administering to the subject an amount of the provided pharmaceutical composition in an amount effective to treat the infection.

As used herein, "pharmaceutically acceptable" refers to molecular entities and compositions that are physiologically tolerable and do not typically produce an allergic or similar untoward reaction, such as gastric upset, dizziness and the like, when administered to a human. A pharmaceutically acceptable carrier encompasses any of the standard pharmaceutically accepted carriers, such as phosphate buffered saline solution, water emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The invention also provides for pharmaceutical compositions capable of inhibiting S. aureus infection together with suitable diluents, preservatives, solubilizers, emulsifiers and adjuvants. Other embodiments of the compositions of the invention incorporate particulate forms, protective coatings, protease inhibitors or permeation enhancers for various routes of administration, including but not limited to intravenous, intramuscular, parenteral, pulmonary, nasal and oral.

As used herein, an "effective amount" is the amount required to achieve a clinically significant reduction in S. aureus infection, preferably of at least 30 percent, more preferably of at least 50 percent, most preferably of at least 90 percent. Accordingly, the effective amount will vary with the subject being treated, as well as the condition to be treated. For the purposes of this invention, the methods of administration are to include, but are not limited to administration cutaneously, subcutaneously, intravenously, parenterally, orally, topically, or by aerosol.

The present invention further contemplates therapeutic compositions useful in practicing the therapeutic methods of this invention. A subject therapeutic composition includes, in admixture, a pharmaceutically acceptable excipient (carrier) and one or more of a polypeptide analog or fragment of the provided peptide or peptide composition, a peptidomimetic composition thereof as described herein as an active ingredient. A cocktail of the provided pharmaceutical composition in various combinations is also contemplated.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

As used herein, "pM" means picomolar, "nM" means nanmolar, "uM, means micromolar, "mM" means millimolar, "ul" or "$\mu l$" mean microliter, "ml" means milliliter, "l" means liter.

As used herein, the term "synthetic amino acid" means an amino acid which is chemically synthesized and is not one of the 20 amino acids naturally occurring in nature.

As used herein, the term "biosynthetic amino acid" means an amino acid found in nature other than the 20 amino acids commonly described and understood in the art as "natural amino acids." Examples of "non-amide isosteres" include but are not limited to secondary amine, ketone, carbon-carbon, thioether, and ether moieties.

As used herein, the term "non-natural peptide analog" means a variant peptide comprising a synthetic amino acid.

As used herein, amino acid residues are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. Abbreviations for amino acid residues are used in keeping with standard polypeptide nomenclature delineated in *J. Biol. Chem.*, 243:3552–59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Amino acids with nonpolar R groups include: Alanine, Valine, Leucine, Isoleucine, Proline, Phenylalanine, Tryptophan and Methionine. Amino acids with uncharged polar R groups include: Glycine, Serine, Threonine, Cysteine, Tyrosine, Asparagine and Glutamine. Amino acids with charged polar R groups (negatively charged at Ph 6.0) include: Aspartic acid and Glutamic acid. Basic amino acids (positively charged at pH 6.0) include: Lysine, Arginine and Histidine (at pH 6.0). Amino acids with phenyl groups include: Phenylalanine, Tryptophan and Tyrosine. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. Amino acids can be in the "D" or "L" configuration. Use of peptidomimetics may involve the incorporation of a non-amino acid residue with non-amide linkages at a given position.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure. The following examples are presented in order to more fully illustrate the preferred embodiments of the invention. They should in no way be construed, however, as limiting the broad scope of the invention. While the invention is described and illustrated herein by references to various specific material, procedures and examples, it is understood that the invention is not restricted to the particular material combinations of material, and procedures selected for that purpose. Numerous variations of such details can be implied as will be appreciated by those skilled in the art.

EXAMPLES

Example 1

Synthesis of a novel class of peptides responsible for *S. aureus* bacterial interference.

The initial synthetic route to the AgrD thiololactone peptides, involving the solution-based cyclization of a thiol ester precursor, proved problematic due to the difficulties associated with the synthesis of the linear starting material. A more efficient strategy was thus developed which involved solid-phase cyclization as the final synthetic step (FIG. 1A). Key to this process was the ability to prepare a fully unprotected peptide immobilized on a solid-support through a reactive thiol ester bond. This was achieved using the recently described 3-mercaptopropionamide-polyethylene glycol-poly-(N,N-dimethylacrylamide) [HS-PEGA] support (Camarero, J. A., 1998) in combination with Boc-solid phase peptide synthesis (SPPS) (Schnolzer, M., et al., 1992). The acid stability of the alkyl-thiol ester linkage between the peptide and the resin means that the completed peptide can be globally deprotected without being cleaved from the support. Generation of the desired thiololactone-peptide is then achieved by simply swelling the peptide-resin beads in aqueous buffer at pH 7.0, resulting in a chemoselective intramolecular cyclization/cleavage reaction. Note that this final step is made possible due to the excellent swelling properties of the PEGA support in water (Mendal, M., 1992).

Figure 1B:
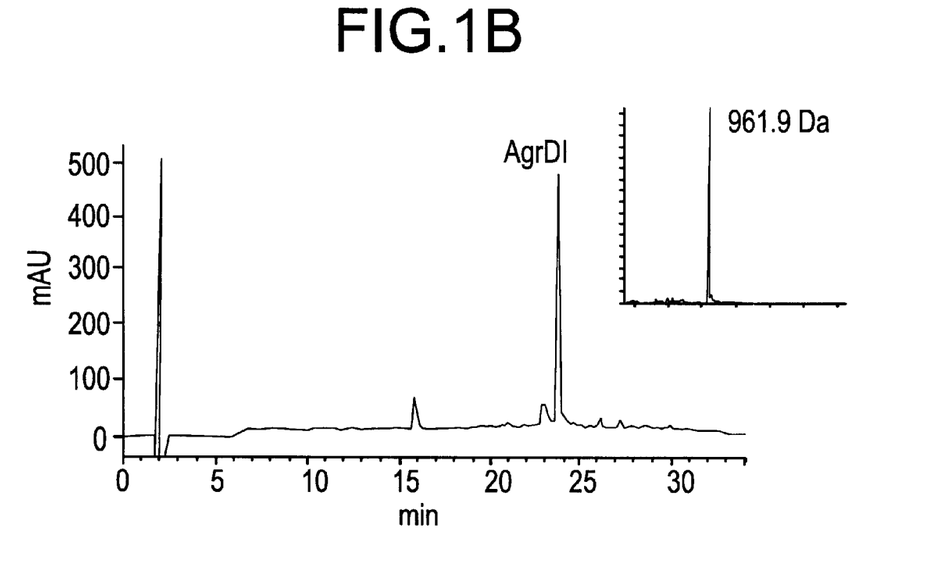
FIG. 1B. Reverse-phase HPLC of the crude reaction mixture from the AgrDI peptide synthesis. Inset shows the electrospray mass spectrum (ESMS) obtained from the major component in the mixture: Expected mass for the AgrDI thiololactone= 962.374 Da (961.9 mass).
Figure 1C:
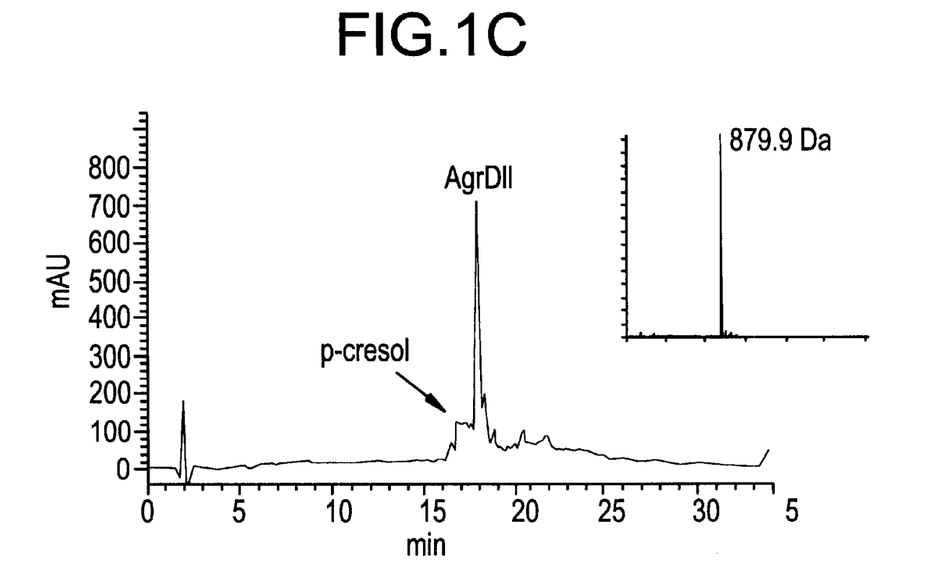

The synthetic approach illustrated in FIG. 1A was used to prepare peptides AgrDI and AgrDII from *S. aureus* group I and group II strain sequence of the group III AgrD peptide has not yet been established at the time of the present invention). In each case, the final cyclization/cleavage reaction was found to be remarkably clean giving rise to a single major component in excellent yield (FIG. 1B). Following purification, the ligation products were characterized as being the expected thiololactone-peptides by electrospray mass spectrometry, chemical reactivity to neutral hydroxylamine (Chou, T. C. and Lipmann, F, 1952) and two-dimensional $^1$H nuclear magnetic resonance (NMR) spectroscopy (Bax, A., et al., 1985; Wuthrich, K, 1986). (Peptide thiol esters react rapidly with neutral hydroxylamine to give the corresponding hydroxamate derivatives).

Figure 2A:
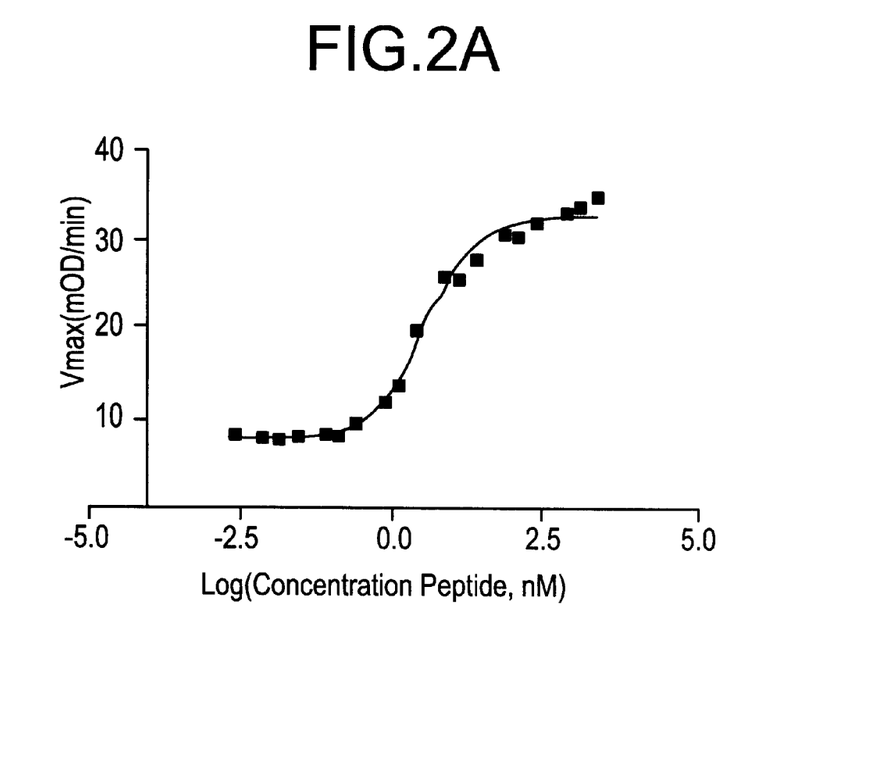
FIG. 2A. Activation of the agr response in group II *S. aureus* cells by synthetic AgrDII.
Figure 2B:
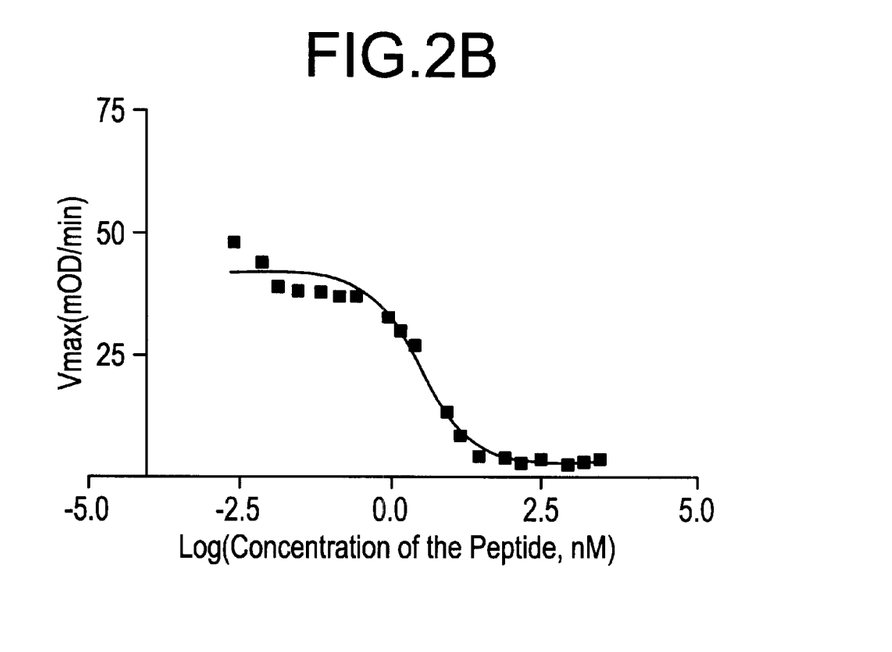
FIG. 2B. Inhibition of the agr response in group I *S. aureus* cells by synthetic AgrDII.

The biological activity of the synthetic AgrDI and AgrDII peptides was assayed using cultured *S. aureus* strains containing a β-lactamase reporter gene fused to the agrP3 promoter (Novick, R. P., et al., 1995). This allowed activation or inhibition of the agr response to be monitored spectrophotometrically using a calorimetric β-lactamase activity assay (Table 1). As with their naturally derived counterparts, synthetic AgrDI and AgrDII were found to activate the agr response only within their own *S. aureus* class, and inhibit the agr response only in *S. aureus* strains from the other two classes (Table 1). Further studies revealed a dose-dependent relationship between the amount of peptide added to the culture supernatant and the degree of activation/inhibition of the agr response (FIGS. 2A–2B). Analysis of the resulting sigmoidal response curves indicated that the ED50 and IC50 values, for activation and inhibition the agr response respectively, were in the low nanomolar range (Table 1). Moreover, these data indicate that there is a critical threshold concentration of the AgrD peptide required for activation of the agr response. This is consistent with the density-sensing/autoinduction mechanism previously proposed (Ji, G., et al., 1997). Importantly, no activation/inhibition activity was detected with linear carboxylate synthetic peptides corresponding to the AgrDI and AgrDII sequences, even at high μM concentrations (Table 1).

TABLE 1

BIOLOGICAL ACTIVITY OF SYNTHETIC AgrD PEPTIDES

| PEPTIDE | $ED_{50}$ Activation (nM) *S. aureus* Group | | | $IC_{50}$ Inhibition (nM) *S. aureus* Group | | |
|---|---|---|---|---|---|---|
| | I | II | III | I | II | III |
| Agr D1 Thiolactone (YSTCDFIM, cyclic thiolactone) | 10.2 | No Activation | No Activation | No Inhibition | 2.9 | 3.2 |
| Agr D2 Thiololactone (GVNACSSLF, cyclic thiolactone) | No Activation | 3.6 | No Activation | 3.4 | No Inhibition | 3.1 |
| Agr D2 Linear Thioester (GVNAASSLF-SR) | No Activation | No Activation | No Activation | No Inhibition | No Inhibition | No Inhibition |
| Agr D2 Linear Free Acid (GVNASSSLF-OH) | No Activation | No Activation | No Activation | No Inhibition | No Inhibition | No Inhibition |
| Agr D2 Lactone (GVNASSSLF, cyclic lactone) | No Activation | No Activation | No Activation | 7.9 | No Inhibition | n/d |

TABLE 1-continued

BIOLOGICAL ACTIVITY OF SYNTHETIC AgrD PEPTIDES

| PEPTIDE | $ED_{50}$ Activation (nM) S. aureus Group | | | $IC_{50}$ Inhibition (nM) S. aureus Group | | |
|---|---|---|---|---|---|---|
| | I | II | III | I | II | III |
| Agr D2 Lactam (structure: HN–GVNAXSSLF cyclized through amide, C=O) | No Activation | No Activation | No Activation | 0.21 | No Inhibition | n/d |

That biological activity is restricted to the thiololactone-peptides, serves to confirm that this unusual posttranslational modification is present within the secreted AgrD peptides.

Example 2
Functional significance of the cyclic ring structure.

Figure 2C:
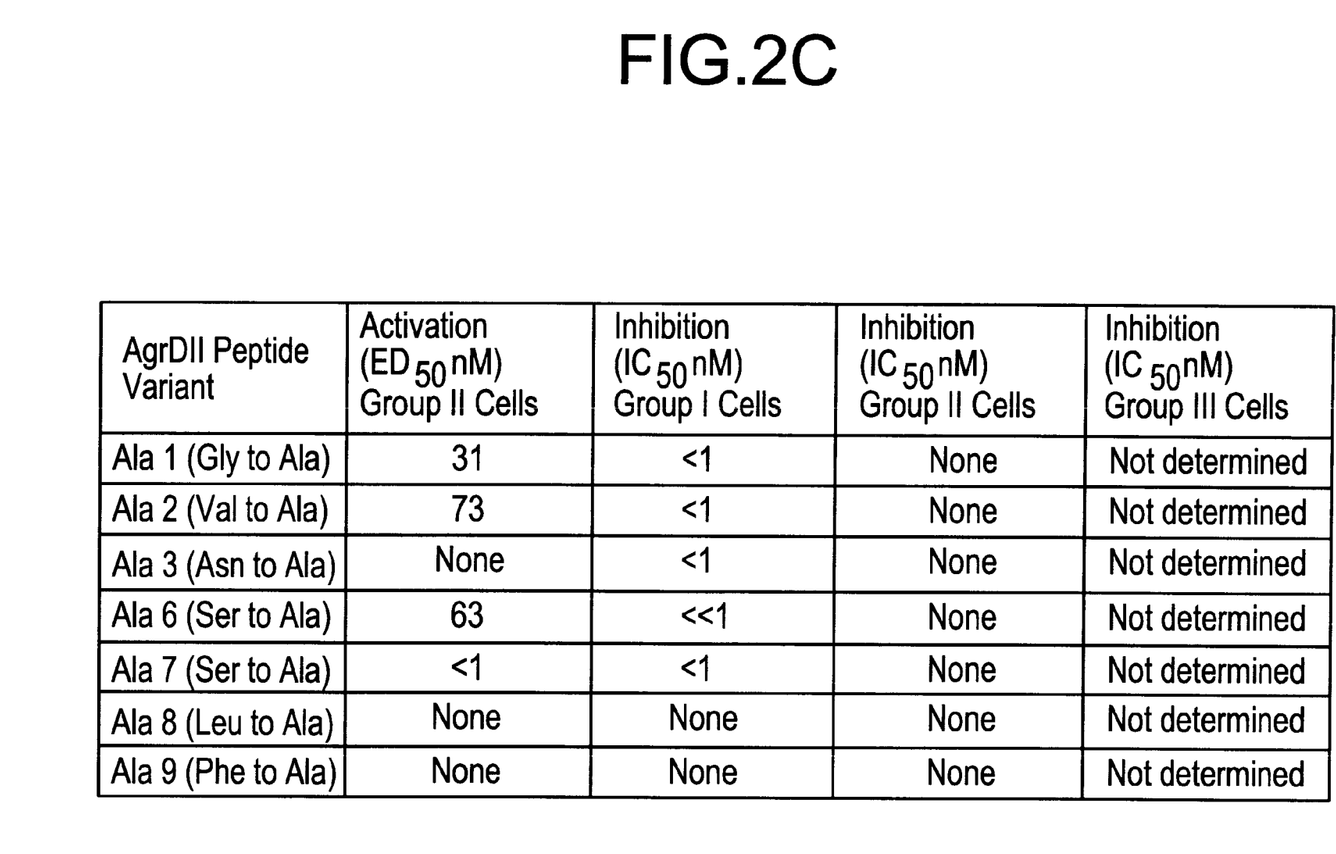
FIG. 2C. Effect of replacing each residue within the AgrDII sequence with alanine on activation and inhibition activity.

The precision and convenience of the synthetic approach makes it possible to systematically vary the chemical structure of the peptides, thus enabling detailed structure-activity studies to be performed. With respect to the AgrD peptides, the initial focus was on the following questions: (i) Which amino acids within the sequence are most important for affinity/selectivity? (ii) What is the role of the thiololactone unit in activation and inhibition of the agr response? To address the first of these issues, an alanine scan was performed on the group II AgrD peptide. Each of the alanine-modified AgrDII peptide variants was prepared and characterized as before, and in each case the purified peptide assayed for its ability to activate or inhibit the agr response in each of the three S. aureus strains. Analysis of the results summarized in FIG. 2C, reveals that there are certain amino acids, residing both within the ring and the tail of the molecules, which are critical for the activation of the agr response (Asn-3, Leu-8, Phe-9). The alanine mutant peptides exhibit a wide activation profile, showing both increases and decreases in activity. In contrast, inhibition of the agr response appears to depend on amino acids only in the ring (Leu-8, Phe-9) and all of the inhibitory alanine-modified AgrDII peptides exhibit increased activity as compared to the wildtype.

The functional significance of the thiololactone structure in the AgrD peptides was investigated through the synthesis of a series of AgrDII variants (Table 1). To address whether a cyclic thiol ester group is strictly required for activity in the native peptide, a linear thiol ester analogue of AgrDII was prepared and assayed (see, Experimental Procedures for detail). As with the linear carboxylate AgrDII variant described earlier, the linear thiol ester peptide was unable to either activate or inhibit the agr response even when added to cultured cells at $\mu M$ concentrations. This result suggests that the cyclic structure present within the AgrD peptides is indispensable for biological activity.

Example 3
Lactone and Lactam variants in the cyclic ring structure provide peptides capable of inhibitory activity without activation activity.

Thiol ester groups are moderately good acylating agents, a property which is utilized in several biological processes (Law, S. K. and A.W. Dodds, 1997; Xu, M.-Q., and F. B. Perler, 1996; Porter, J. A., et al., 1996). It is intriguing to speculate that upon receptor binding, the thiololactone present in the AgrD peptides serves as an acyl donor for the covalent modification of a specific residue within AgrC. The effect of replacing the thiololactone unit in AgrDII with both ester (lactone) and amide moieties (lactam) was of interest. In principle, both of these variants should be significantly less reactive than the thioester peptide ( ), while the lactone variant of AgrDII should also be isosteric to wildtype. Synthesis of the desired AgrDII lactone and lactam variants was achieved via solution cyclization of a partially protected intermediate, followed by global side-chain deprotection. In particular, thiol esters are significantly more reactive towards nitrogen nucleophiles than oxygen esters (Bruice, T. C. and S. J. Benkovic, 1966). As with the linear peptides described above, both the purified lactone and lactam variants were unable to activate the agr response in any of the three S. aureus strains (Table 1). However, both variants are able to inhibit the agr response in groups I and III S. aureus strains. Clearly, the reactive thioester bond is necessary for the activation of the agr response in vivo, however it is not necessary for inhibition.

Analysis of the biological properties of the various AgrDII peptide variants prepared in this study reveals the following: (i) Activation of the agr response is extremely sensitive to both the amino acid sequence and the chemical/stereochemical nature of the AgrD peptide; (ii) Inhibition of the agr response is sensitive to the backbone stereochemistry and the amino acid sequence of the AgrD peptide, but is not affected by changes in the chemical reactivity of the cyclic linkage. These observations suggest that activation and inhibition of the agr response occur through two different mechanisms.

The synthesis of virulence factors and other extracellular proteins responsible for pathogenicity in Staphylococcus aureus is under the control of the agr locus. A secreted agr-encoded peptide, AgrD, is known to be an effector of self-strain activation and cross-strain inhibition of this agr response. Preliminary analysis of AgrD peptides isolated from cultrue supernatants, suggested that they contain an unusual thiol ester-linked cyclic structure. In the present invention, chemical synthesis confirms that these AgrD peptides contains a thiololactone unit, and that this structure is absolutely necessary for full biological activity in the native peptides. Structure-function studies provided by the present invention identify and elucidate key aspects of the peptide structure involved in the differential activation and inhibition functions of the peptides. Novel, non-natural peptide variants are also provided which exhibit no activation activity while retaining (or enhancing) inhibitory activity. Peptides having such properties are useful for treating S. aureus infections.

Discussion

Figure 3A:
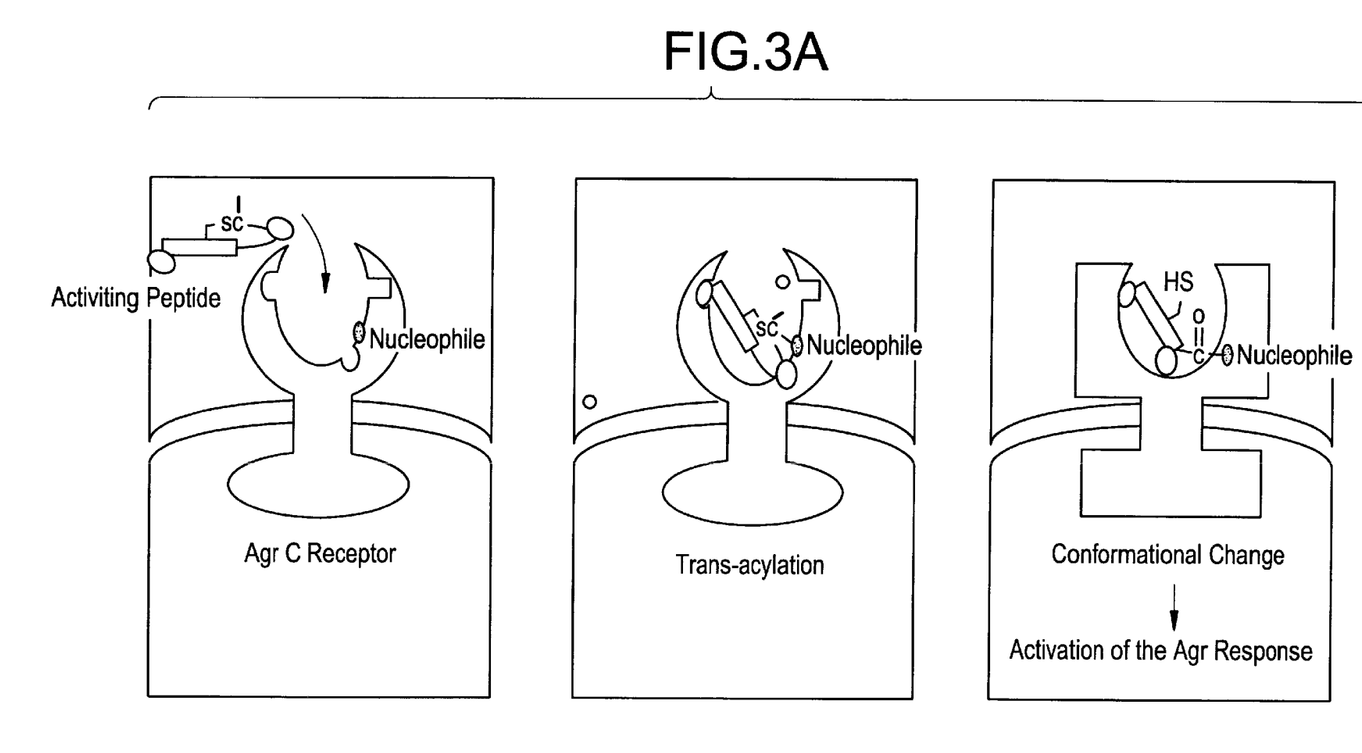
FIG. 3A. Activation of the agr response occurs via an intra-class interaction in which a self AgrD peptide interacts with a self AgrC receptor. Specific AgrD/AgrC interactions lead to proper positioning of the peptide to undergo transacylation with a nucleophile within the receptor, leading to a signal-transducing conformational change.
Figure 3B:
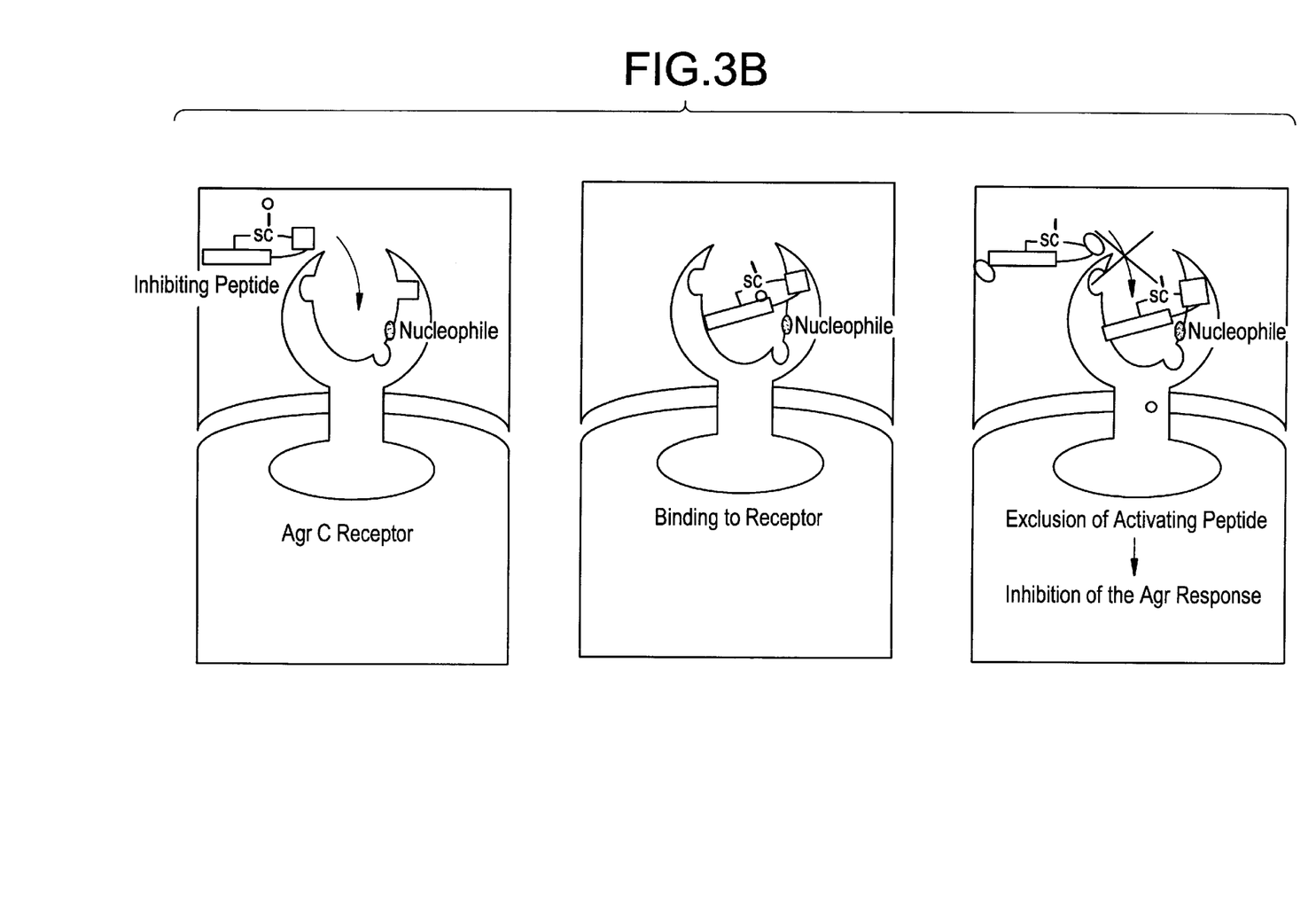
FIG. 3B. Inhibition of the agr response occurs via an inter-class, non-covalent interaction which serves to exclude the strain's own activating peptide from the receptor. This interaction is also specific.

One proposed model in which an AgrD peptide binds its own AgrC receptor (i.e. from the same *S. aureus* class) in a different manner to an AgrC receptor from an another class is illustrated in FIG. 3. This may involve two slightly different orientations of the peptide within the receptor binding pocket, although more than one discrete binding site within the AgrC receptor cannot be excluded. It is further hypothesized that in the intra-class association, highly specific side-chain interactions between AgrC and AgrD result in the thiol ester linkage of the peptide being positioned adjacent to a nucleophilic group within the receptor. This juxtaposition leads to a trans-acylation reaction and activation of the agr response through an associated conformation change in the receptor. The thiol ester linkage is a sufficiently reactive moiety to participate in this trans-acylation step and would explain its presence within the AgrD peptide rather than one of the more common strategies for stereochemical restraint such as a disulfide- or amide-bond formation.

In contrast, no such juxtaposition would be present in the interclass receptor-ligand interaction due to the absence of these specific interactions. Thus the inhibition of the agr response would not involve a signal-transducing trans-acylation step, but rather a non-covalent binding interaction which would serve to exclude the strain's own autoinducing AgrD peptide from the receptor binding pocket. This non-covalent binding interaction does require specific residues, as demonstrated in the alanine-scanning mutagenesis results. It is pertinent to note that the lactone and lactam variants, while being able to inhibit in the appropriate inter-class fashion, do not inhibit self. Inhibition by default, therefore, does not occur when a strain's own autoinducing lactone/lactam variant encounters its own receptor. This evidence further supports the proposed model in which activation and inhibition occur through discrete mechanisms.

In summary, chemical synthesis has been used to confirm the presence of an thiololactone structure within secreted AgrD autoinducing peptides. This highly unusual post-translational modification appears to be mandatory for full biological activity. Based on initial structure-activity studies, it is argued that the thiol ester functionality undergoes a trans-acylation reaction with a specific nucleophile in the AgrC receptor, and that this chemical step is required for activation (but not inhibition) of the agr response. It is also likely that the thiololactone unit limits the in vivo half-life of the peptide—the thiol ester linkage will undergo slow hydrolysis at physiological pH leading to the generation of an inactive linear peptide. The biological significance of this short-term in vivo efficacy is as yet unknown. It is equally unknown what role (if any) the recently reported 38 KDa RAP protein (Balaban, N., et al., 1998) plays in activation of the agr response by the secreted AgrD peptides.

Ready synthetic access to AgrD peptides represents an important step towards using the agr autoinduction system as a route to novel therapeutic agents. Indeed, the observation that it is possible to prepare novel synthetic AgrD variants which are capable of inhibiting but not activating the agr response is particularly significant in this regard. Moreover, the ability to easily adapt a solid-phase synthetic strategy to combinatorial-type synthesis is advantageous in the rapid identification of interesting compounds.

Experimental Procedures:

Biological activity of synthetic AgrD peptides. Biological assays were performed using groups I (RN6390B), II (SA502A) and III (RN8463) *S. aureus* strains (Ji, G., et al., 1997), each containing an agr P3-blaZ fusion plasmid (Novick, R. P., et al., 1995). Cells were grown in CYGP medium at 37° C. to either early exponential phase for agr activation studies, or midexponential phase for agr inhibition studies. To the cultured cells were then added either buffer solution (negative control), the appropriate cell supernatant containing the natural AgrD peptide as prepared as in (Ji, G., et al., 1995) (positive control) or the synthetic peptide solution in 20 mM tris.HCl buffer at pH 6.0. The cultures were then incubated at 37° C. with shaking for either 55 minutes (activation) or 80 minutes (inhibition) and β-lactamase activity then assayed using the nitrocefin spectrophotometric method modified as described in (Novick, R. P., et al., 1995) $ED_{50}$ and $IC_{50}$ values were extracted from the sigmoidal dose-response curves (e.g. FIGS. 2A–2B) using the program PRISM (GRAPHPAD Software Inc., San Diego, Calif.). All assays were performed in triplicate and the $ED_{50}$ and $IC_{50}$ values agreed to within ±10%.

Thioesterification studies.

Initial studies involved selective thioesterification of a linear a-thiol acid peptide with 5,5'-dithiobis(2-nitrobenzoic acid) to give the S-(5-sulfenyl-2-nitrobenzoic acid) α-thiol ester derivative. This linear thiol ester precursor was then cyclized in solution through transthioesterification involving the cyteine sulfhydryl group. The overall yields using this strategy were poor, principally because of difficulties in selectively esterifying the α-thiol peptide.

Peptide synthesis.

All peptides were synthesized manually according to the in situ neutralization/HBTU activation protocol for Boc SPPS (M. Schnolzer, P. Alewood, A. Jones, D.Alewood, B. H. Kent, *Int. J. Pept. Protein Res.* 40: 180–193 (1992). Thiololactone AgrD peptides were assembled on pre-loaded Boc-AA-[COS]-PEGA resins (Camarero, J. A., et al., 1998). Following chain assembly, peptides were treated with HF for 1 hour at 0° C. to give the corresponding fully unprotected peptide-[COS]-PEGA resins which were then washed with cold diethyl ether and then $CH_3CN/H_2O$ containing 0.1% trifluoroacetic acid. Unprotected peptides were chemoselectively cyclized and simultaneously cleaved from the support by swelling the beads in a mixtture of 0.1 M sodium phosphate buffer at pH 7.0 and acetonitrile (80:20). After 12 hours rection, the beads were removed by filtration, washed with 0.1% trifluoroacetic acid in water and the peptides purified from the filtrate by reverse-phase HPLC.

Assembly of Peptides on resin.

The peptide GVNAASSLF was assembled on an HS-PEGA resin (Camarero, et al., 1998) using Boc-SPPS. This corresponds to the AgrDII sequence with the single cysteine residue mutated to an alanine. Following synthesis and global deprotection, the peptide-[COS]-PEGA beads were swollen in a buffer containing 0.1 M sodium phosphate, pH 7.0 and ethanethiol (2% v/v), and the cleavage reaction allowed to proceed for 3 hours. The desired ethyl α thiol ester peptide was then purified from the supernatant by reverse-phase HPLC.

Protected peptides

The protected peptides Z-Gly-Val-Asn-Ala-Ser(ᵗBu)-Ser(Bzl)-Ser(Bzl)-Leu-Phe and Z-Gly-Val-Asn-Ala-Dapa(Boc)-Ser(Bzl)-Ser(Bzl)-Leu-Phe corresponding to the Agr-DII sequence with a Cys5 to Ser mutation (lactone) and a Cys5 to Dapa (Diaminopropionic acid) (lactam) respectively, were synthesized on a Wang-resin using an Fmoc Nα protection strategy with HBTU activation protocols. Following chain assembly, the peptides were cleaved from the support and the Ser-5 or Dapa-5 side-chain deprotected by treatment with a trifluoroacetic acid: anisole:water mixture (90:5:5) for 4 hours. The partially protected peptide-α carboxylates were then dissolved in DMF (0.5 mg/mL) and treated with PyBOP (5 eq.) (and a catalytic amount of dimethylaminopyridine for the lactone precursor). The cyclization reaction was monitored by HPLC which indicated a period of 2 hours to be sufficient for complete reaction. The remaining protecting groups were then removed by treatment with HF and the desired peptides purified by reverse-phase HPLC and characterized by mass spectometry and 2D $^1$H NMR spectroscopy.

NMR

Two-dimensional $^1$H NMR spectra were measured on a Bruker DPX-400 spectrometer. Peptides were dissolved in either dimethylsulfoxide-d6 or 9:1 H2O/D2O pH 4.0 to a final concentration of 1–2 mM and a series of TOCSY (A. Bax, D.G. Davis, *J Magn. Reson.* 65: 355–360 (1985) and ROESY experiments recorded at 278 K. $^1$H resonances were assigned using standard procedures (K. Wuthrich, *NMR of Proteins and Nucleic Acids* (Wiley, New York, 1986).

REFERENCES

The following is a list of documents related to the above disclosure and particularly to the experimental procedures and discussions. The documents should be considered as incorporated by reference in their entirety.

1. Balaban, N., et al., *Science* 280:438–440 (1998).
2. Bax, A. and D. G. Davis, *J. Magn. Reson.* 655:355–360 (1985)
3. Buice, T. C. and S. J. Benkovic, in *Bioorganic Mechanisms* 1:259–297 (Benjamin, New York, 1966).
4. Camarero, G. C., et al., *J. Peptide Res.* 51:303–316 (1998).
5. Chou, T. C. and F. Lippmann, *J. Biol. Chem.* 196:89 (1952).
6. Ji, G., et al., *Proc. Natl. Acad. Sci. USA* 92:12055–12059 (1995).
7. Ji, G., et al., *Science* 276:2027–2030 (1997).
8. Law, S. K., and A. W. Dodds, *Protein Science* 6:263–274 (1997).
9. Mendal, M. *Tetrahedron Lett.* 33:3077–3080 (1992).
10. Morfeldt, E., et al., *EMBO J.* 14:4569–4577 (1995).
11. Muir, T. W., et al., *Chemistry and Biology* 3:817–825 (1996).
12. Novick, R. P., et al., *Mol. Gen. Genet.* 248:446–458 (1995).
13. Novick, R. P., et al., *EMBO J.* 12:3967–3975 (1993).
14. Porter, J. A., et al., *Science* 274:255–259 (1996).
15. Schnolzer, M., et al., *Int. J. Pept. Protein Res.* 40:180–193 (1992).
16. Wuthrich, K, *NMR of Proteins and Nucleic Acids* (Wiley, New York, 1986).
17. Xu, M.-Q., and F. B. Perler, *EMBO J.* 15:5146–5153 (1996).

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A cyclic peptide comprising the structure:

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10.

2. A cyclic peptide comprising the amino acid sequence of $NH_2$—$X_{(n)}$—Z—$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10.

3. The cyclic peptide of claim 2, wherein Z has a side chain comprising oxygen, nitrogen or carbon.

4. The cyclic peptide of claim 2, wherein the cyclic bond is a lactam or lactone bond.

5. The cyclic peptide of claim 1, wherein y is 4.

6. The cyclic peptide of claim 2, wherein y is 4.

7. The cyclic peptide of claim 5, wherein the peptide is selected from the group of peptides having an amino acid sequence that comprises G-V-N-A-X-S-S-L-F (Seq.ID No.:1), G-A-N-A-X-S-S-L-F (Seq.ID No.:2), G-V-A-A-X-S-S-L-F (Seq.ID No.:3), A-V-A-N-X-S-S-L-F (Seq.ID No.:4), G-V-N-A-X-A-S-L-F (Seq.ID No.:5), G-V-N-A-X-S-A-L-F (Seq.ID No.:6), G-V-N-A-X-S-S-A-F (Seq.ID No.:7), and X-S-S-L-F (Seq.ID No.:8).

8. The cyclic peptide of claim 6, wherein the peptide is selected from the group of peptides having an amino acid sequence that comprises G-V-N-A-X-S-S-L-F (Seq.ID No.:1), G-A-N-A-X-S-S-L-F (Seq.ID No.:2), G-V-A-A-X-S-S-L-F (Seq.ID No.:3), A-V-A-N-X-S-S-L-F (Seq.ID No.:4), G-V-N-A-X-A-S-L-F (Seq.ID No.:5), G-V-N-A-X-S-A-L-F (Seq.ID No.:6), G-V-N-A-X-S-S-A-F (Seq.ID No.:7), and X-S-S-L-F (Seq.ID No.:8).

9. A composition comprising the peptide of claim 1 and a carrier.

10. A composition comprising the peptide of claim 2 and a carrier.

11. A pharmaceutical composition comprising the peptide of claim 1 and a pharmaceutically acceptable carrier.

12. A pharmaceutical composition comprising the peptide of claim 2 and a pharmaceutically acceptable carrier.

13. The pharmaceutical composition of claim 11, wherein the carrier is selected from the group consisting of a diluent, an aerosol, a topical carrier, an aqueous solution, a nonaqueous solution, and a solid carrier.

14. The pharmaceutical composition of claim 12, wherein the carrier is selected from the group consisting of a diluent, an aerosol, a topical carrier, an aqueous solution, a nonaqueous solution, and a solid carrier.

15. A method for the preparation of a cyclic peptide comprising the structure:

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10, said method comprising:

A. assembling the linear constituents of the peptide under preparation on a polyethylene glycol polyacrylamide (PEGA) resin support to form a protected and bound peptide chain;

B. treating the peptide chain of Step A to cause deprotection thereof;

C. treating the deprotected peptide of Step B with buffer at a neutral pH for a period of time sufficient to cleave said peptide from said solid phase support and to form said cyclic peptide; and D. recovering said cyclic peptide.

16. A method for the preparation of a cyclic peptide in accordance with claim 1, which comprises:

A. assembling the linear peptide chain corresponding in composition to said cyclic peptide on to a solid phase resin support containing 3-mercapto-propionamide-polyethylene glycol-poly-($N_1N_4$-dimethacrylamide) (HS-PEGA) to form a protected assembled peptide;

B. treating the protected assembled peptide of Step A to deprotect said assembled peptide;

C. treating the deprotected peptide of Step B with aqueous buffer at a pH of about 7.0 for a period of time sufficient to form said cyclic peptide and to cleave said peptide from said solid phase resin support; and D. recovering said cyclic peptide.

17. The method of claim 15, wherein said solid phase resin support comprises tertbutyloxycarbonyl-amino acid-(BOC-AA)-(linear assembled peptide)-polyethylene glycol polyacrylamide (PEGA).

18. The method of claim 15, wherein the treatment of Step B is performed with hydrofluoric acid (HF) for about 1 hour.

19. The method of claim 15, wherein the treatment of Step C is performed with a buffer comprising $Na_2PO_4$ and acetonitride.

20. The method of claim 19, wherein the treatment of Step C is performed for about 12 hours.

* * * * *

SEQUENCE LISTING

```
<160> NUMBER OF SEQ ID NOS:  8

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 1

Gly Val Asn Ala Xaa Ser Ser Leu Phe
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 2

Gly Ala Asn Ala Xaa Ser Ser Leu Phe
  1               5

<210> SEQ ID NO 3
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 3

Gly Val Ala Ala Xaa Ser Ser Leu Phe
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 4

Ala Val Asn Ala Xaa Ser Ser Leu Phe
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 5

Gly Val Asn Ala Xaa Ala Ser Leu Phe
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 6

Gly Val Asn Ala Xaa Ser Ala Leu Phe
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (5)
<223> OTHER INFORMATION: Xaa represents any amino acid at this position.

<400> SEQUENCE: 7
```

```
Gly Val Asn Ala Xaa Ser Ser Ala Phe
  1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: VARIANT
<222> LOCATION: (1)
<223> OTHER INFORMATION: Xaa represents any amino acid at this position.

<400> SEQUENCE: 8

Xaa Ser Ser Leu Phe
  1               5
```